US008648204B2

(12) United States Patent
Amari et al.

(10) Patent No.: US 8,648,204 B2
(45) Date of Patent: Feb. 11, 2014

(54) 1-PHENYL-2-PYRIDINYL ALKYL ALCOHOL COMPOUNDS AS PHOSPHODIESTERASE INHIBITORS

(71) Applicant: Chiesi Farmaceutici S.p.A., Parma (IT)

(72) Inventors: Gabriele Amari, Parma (IT); Elisabetta Armani, Parma (IT); Maurizio Delcanale, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/930,304

(22) Filed: Jun. 28, 2013

(65) Prior Publication Data

US 2013/0289010 A1 Oct. 31, 2013

Related U.S. Application Data

(60) Division of application No. 13/618,346, filed on Sep. 14, 2012, which is a continuation of application No. 12/700,926, filed on Feb. 5, 2010, now Pat. No. 8,440,834.

(30) Foreign Application Priority Data

Feb. 6, 2009 (EP) .................................. 09001660

(51) Int. Cl.
*C07D 211/82* (2006.01)
*A61K 31/435* (2006.01)
(52) U.S. Cl.
USPC ........................................ 546/329; 514/277
(58) Field of Classification Search
None
See application file for complete search history.

(56) References Cited

U.S. PATENT DOCUMENTS

| | | | |
|---|---|---|---|
| 5,712,298 A | 1/1998 | Amschler | |
| 7,671,066 B2 | 3/2010 | Amari et al. | |
| 7,820,698 B2 | 10/2010 | Rizzi et al. | |
| 7,923,565 B2 | 4/2011 | Delcanale et al. | |
| 7,968,724 B2 | 6/2011 | Armani et al. | |
| 8,203,000 B2 | 6/2012 | Delcanale et al. | |
| 2009/0048220 A1 | 2/2009 | Delcanale et al. | |
| 2009/0170903 A1 | 7/2009 | Armani et al. | |
| 2010/0204256 A1 | 8/2010 | Amari et al. | |
| 2011/0144075 A1 | 6/2011 | Delcanale et al. | |
| 2012/0031403 A1 | 2/2012 | Cocconi et al. | |
| 2012/0034172 A1 | 2/2012 | Bonelli et al. | |
| 2012/0116091 A1 | 5/2012 | Delcanale et al. | |
| 2013/0005716 A1 | 1/2013 | Armani et al. | |
| 2013/0079313 A1 | 3/2013 | Armani et al. | |
| 2013/0102576 A1 | 4/2013 | Armani et al. | |
| 2013/0137648 A1 | 5/2013 | Delcanale et al. | |

FOREIGN PATENT DOCUMENTS

| | | |
|---|---|---|
| WO | 95/01338 | 1/1995 |
| WO | 2008/006509 | 1/2008 |
| WO | 2009/018909 | 2/2009 |

OTHER PUBLICATIONS

Odingo, J.O., Expert Opinion on Therapeutic Patents, Informa Healthcare, GB, vol. 15, No. 7, 2005, pp. 773-787.
U.S. Appl. No. 13/909,222, filed Jun. 4, 2013, Armani, et al.

*Primary Examiner* — Janet L Andres
*Assistant Examiner* — Heidi Reese
(74) *Attorney, Agent, or Firm* — Oblon, Spivak, McClelland, Maier & Neustadt, L.L.P.

(57) ABSTRACT

1-Phenyl-2-pyridinyl alkyl alcohol compounds are effective as inhibitors of the phosphodiesterase 4 (PDE4) enzyme and may be used to prevent and/or treat certain diseases or conditions.

21 Claims, 1 Drawing Sheet

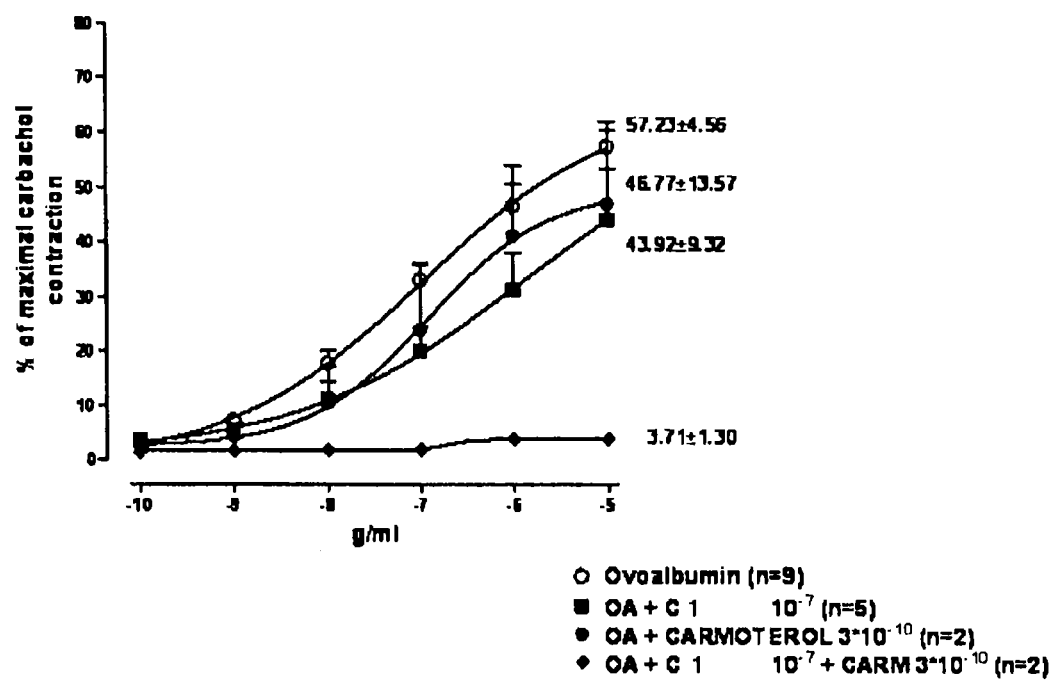

1-PHENYL-2-PYRIDINYL ALKYL ALCOHOL COMPOUNDS AS PHOSPHODIESTERASE INHIBITORS

CROSS REFERENCES TO RELATED APPLICATIONS

This application is a Divisional Application of U.S. patent application Ser. No. 13/618,346, filed on Sep. 14, 2012, which was a continuation of U.S. patent Ser. No. 12/700,926, filed on Feb. 5, 2010, now U.S. Pat. No. 8,440,834, and claims priority to European Patent Application No. 09001660.1, filed on Feb. 6, 2009, which is incorporated herein by reference in its entirety.

BACKGROUND OF THE INVENTION

1. Field of the Invention

The present invention relates to inhibitors of the phosphodiesterase 4 (PDE4) enzyme. More particularly, the invention relates to 1-phenyl-2-pyridinyl alkyl alcohol compounds, which are useful as inhibitors of the phosphodiesterase 4 (PDE4) enzyme. The present invention also relates to processes for the preparation of such compounds, compositions which comprise such a compound, and combinations of such compounds. The present invention further relates to therapeutic uses of such compounds.

2. Discussion of the Background

Airway obstruction characterizes a number of severe respiratory diseases, including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, avoiding any systemic side-effects, thus providing a more rapid clinical response and a higher therapeutic ratio.

Inhaled corticosteroids are the current maintenance therapy of choice for asthma and together with bronchodilator $\beta_2$-agonists for acute symptom relief, they form the mainstay of current therapy for the disease. The current management of COPD is largely symptomatic by means of bronchodilating therapy with inhaled anticholinergics and inhaled $\beta_2$-adrenoceptor agonists. However, corticosteroids do not reduce the inflammatory response in COPD as they do in asthma.

Another class of therapeutic agents which are under investigation in view of its anti-inflammatory effects for the treatment of inflammatory respiratory diseases such as asthma and COPD is represented by the inhibitors of the phosphodiesterase enzymes (PDEs), in particular of the phosphodiesterase type 4 (hereinafter referred to as PDE4).

Various compounds acting as PDE4 inhibitors have been disclosed. However, the usefulness of several PDE4 inhibitors of the first-generation such as rolipram and piclamilast has been limited because of their undesirable side effects such as nausea, gastric acid secretion and emesis due to their action on PDE4 in the central nervous system and due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (see, Jacobitz, S et al., Mol. Pharmacol., 1996, 50, 891-899), which is found in the immune and inflammatory cells. While both forms appear to exhibit catalytic activity, they differ with respect to their sensitivity to inhibitors. In particular, compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as cilomilast and roflumilast. However, even these compounds are not provided with a good selectivity towards LPDE4.

Compounds with selective LPDE4 inhibition activity are disclosed in WO2009/018909 (PCT/EP2008/005843).

1-phenyl-2-pyridinyl alkylen alcohols and their use as PDE4 inhibitors are also described in WO 2008/006509.

However, there remains a need for compounds with improved selective LPDE4 inhibition activity.

SUMMARY OF THE INVENTION

Accordingly, it is one object of the present invention to provide novel compounds with selective LPDE4 inhibition activity.

It is another object of the present invention to provide novel methods of preparing such a compound.

It is another object of the present invention to provide novel intermediates useful in the preparation of such a compound.

It is another object of the present invention to provide novel pharmaceutical compositions which contain such a compound.

It is another object of the present invention to provide novel methods of treating and/or preventing certain diseases and conditions by administering such a compound.

It is another object of the present invention to provide novel methods of preventing and/or treating allergic rhinitis.

It is another object of the present invention to provide novel methods of preventing and/or treating of atopic dermatitis.

These and other objects, which will become apparent during the following detailed description, have been achieved by the inventors' discovery that compounds of formula (I) as (−) enantiomers act as inhibitors of the phosphodiesterase 4 (PDE4) enzyme:

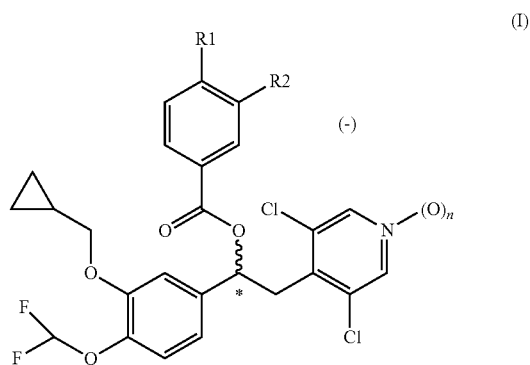

wherein:
n is 0 or 1;
R1 and R2 may be the same or different, and are independently selected from the group consisting of:
linear or branched $C_1$-$C_6$ alkyl, optionally substituted by one or more halogen atoms;

—OR3 wherein R3 is a linear or branched $C_1$-$C_6$ alkyl optionally substituted with one or more halogen atoms or $C_3$-$C_7$ cycloalkyl groups; and —NHSO$_2$R4 wherein R4 is a linear or branched $C_1$-$C_4$ alkyl optionally substituted with one or more halogen atoms, wherein at least one of R1 and R2 is —NHSO$_2$R4.

The invention also encompasses the pharmaceutically acceptable hydrates, solvates, addition complexes, inorganic or organic salts thereof, e.g. sodium, potassium and lysine salts.

The present invention also provides a process for the preparation of the compounds of formula (I) as reported in Scheme 1 (below), which comprises reacting aldehyde (1) with methyldichloropyridine (2) to obtain racemic alcohol (3). This latter is then condensed with a chiral acid such as (S)-naproxen or (S)-acetylmandelic acid to obtain a diastereomeric mixture (10) or (5), respectively, as per routes 1 or 2 of scheme 1. Separation into the single diastereoisomers respectively (11) and (13) or (6) and (8) is carried out by chromatography, crystallization or other well known methods, giving after cleavage, respectively enantiomeric alcohols (−) (12) and (+) (14) or (+) (7) and (−) (9). Finally, by reaction with a suitable benzoic acid (15), enantiomers (+) (14) or (+) (7) give compounds of general formula (I).

The present invention also provides a process for the preparation of compounds of formula (I) wherein n is 0 as reported in Scheme 1 (below), which comprises the reaction of any enantiomeric alcohol, for instance (+) (14), with a benzoic acid (15).

The present invention also provides a process for the preparation of compounds of formula (I) wherein n is 1 as reported in Scheme 1 (below), which comprises the oxidization of enantiomeric alcohol (+) (14) by means of an oxidizing agent such as 3-chloroperbenzoic acid, peracetic acid or hydrogen peroxide to obtain the alcohol (+) enantiomer (7), which by reaction with a benzoic acid of formula (15) gives compounds of formula (I) wherein n is 1.

The present invention also provides a process for the preparation of compounds of formula (I) wherein n is 1 as reported in Scheme 1 below), which comprises the oxidization of esters of formula (I) wherein n is 0 by means of an oxidizing agent such as 3-chloroperbenzoic acid, peracetic acid or hydrogen peroxide.

The present invention also provides intermediate compounds of general formula (II)

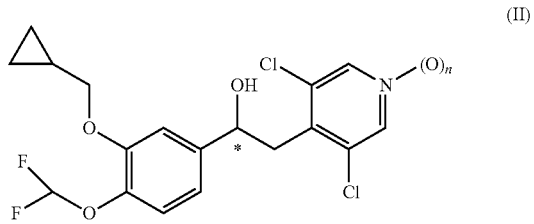

(II)

wherein n is as defined above and the carbon atom represented with an asterisk has the (S) configuration.

The present invention also provides pharmaceutical compositions comprising a compound of formula (I) and one or more pharmaceutically acceptable carriers and/or excipients.

The present invention in particular provides pharmaceutical preparations suitable for administration by inhalation.

The present invention also provides combinations of a compound of formula (I) with a second component selected from the classes of long-acting $\beta_2$ agonists, M3 antagonists and corticosteroids.

The present invention also provides combinations of a compound of formula (I) with a long-acting $\beta_2$ agonist selected from the group consisting of carmoterol, GSK-642444, indacaterol, mil veterol, arformoterol, formoterol, salbutamol, formoterol, levalbuterol, terbutaline, AZD-3199, BI-1744-CL, LAS-100977, bambuterol, isoproterenol, procaterol, clenbuterol, reproterol, fenoterol, and ASF-1020.

The present invention also provides combinations of a compound of formula (I) with a M3 antagonist selected from the group consisting of aclidinium, tiotropium, ipratropium and oxitropium.

The present invention also provides combinations of a compound of formula (I) with a corticosteroid selected from the group consisting of dexamethasone, fluticasone, fluticasone furoate, prednisolone, betamethasone, budesonide, mometasone, mometasone furoate, triamcinolone acetonide, ciclesonide, TPI-1020, beclomethasone, beclomethasone dipropionate, prednisone, deflazacort, hydrocortisone, QAE-397, and flunisolide.

In a preferred embodiment, the present invention provides combinations of a compound of formula (I) with formoterol or carmoterol.

The present invention also provides compounds of formula (I) for use as a medicament.

Also provided is the use of the compounds of formula (I) in the preparation of a medicament for the prevention or treatment of any disease wherein the activity of PDE4 receptors is implicated and inhibition of PDE4 receptor activity is desired.

The present invention also provides a method for the prevention or treatment of any disease wherein the activity of PDE4 receptors is implicated and inhibition of PDE4 receptor activity is desired, which methods comprises administering to a patient in need thereof a therapeutically effective amount of a compound of formula (I).

The above uses or methods comprise a compound of formula (I) either alone or combined with other active ingredients among those formerly reported.

The above diseases wherein the activity of PDE4 receptors and inhibition of PDE4 receptors are implicated, comprise diseases of the respiratory tract, characterized by airway obstruction such as astma and COPD.

The present invention also provides methods of preventing and/or treating allergic rhinitis.

The present invention also provides methods of preventing and/or treating of atopic dermatitis.

Furthermore, the invention also provides the use of the compounds of formula (I) for the in vitro inhibition of PDE4.

The invention also provides devices which may be a single- or multi-dose dry powder inhaler, a metered dose inhaler or a soft mist nebulizer comprising a compound of formula (I).

The invention also provides kits comprising the pharmaceutical compositions of compounds of formula (I), alone or in combination with an additional pharmaceutical ingredient, in admixture with one or more pharmaceutically acceptable carriers and/or excipients, and a device which may be a single- or multi-dose dry powder inhaler, a metered dose inhaler or a soft mist nebulizer.

The present invention provides a set of potent novel PDE4 inhibitors having excellent LPDE4 selectivity.

Surprisingly, it has been found that the presence of sulphonamido substituents on the benzoate residue markedly improves the potency.

Moreover, it has been surprisingly found that the sulphonylamido derivatives of the invention, which are (−) enantiomers (see, the carbon atom marked with an asterisk) are more potent than the corresponding (+) enantiomers and racemates.

It has now been found that an unexpectedly beneficial therapeutic effect, particularly a synergistic effect, is obtained in the treatment of inflammatory or obstructive diseases of the respiratory tract when the compounds of the invention are used in combination with a long-acting $\beta_2$-agonist.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 is a graph which shows the existence of a synergic action for a preferred embodiment of the present invention.
OA=ovoalbumin
C1=3-Cyclopropylmethoxy-4-methanesulfonylamino-benzoic acid 1-(3-cyclopropylmethoxy-4-difluoromethoxy-phenyl)-2-(3,5-dichloro-pyridin-4-yl)-ethyl ester
CARM=carmoterol

DETAILED DESCRIPTION OF THE PREFERRED EMBODIMENTS

The term "halogen atoms" as used herein includes fluorine, chlorine, bromine and iodine.

As used herein, the expression "linear or branched $C_1$-$C_x$ alkyl" where x is an integer greater than 1, such as $C_1$-$C_6$ or $C_1$-$C_4$ alkyl, refers to straight or branched chain alkyl groups wherein the number of carbon atoms is in the range 1 to x (e.g. 1 to 6 or 1 to 4). Examples of alkyl groups may thus include methyl, ethyl, n-propyl, isopropyl, t-butyl, pentyl, hexyl and the like.

Optionally in said groups one or more hydrogen atoms can be replaced by halogen atoms, preferably chlorine or fluorine.

As used herein, the expression "$C_3$-$C_7$ cycloalkyl" refers to cyclic non-aromatic hydrocarbon groups containing 3 to 7 ring carbon atoms. Examples of them may thus include cyclopropyl, cyclobutyl, cyclopentyl, cyclohexyl and cycloheptyl.

Unless otherwise provided, when referring to chiral compounds, a degree of purity "substantially pure" here means at least greater than about 97% chirally pure, preferably greater than 99% and most preferably greater than 99.9%.

The invention is directed to compounds acting as inhibitors of the phosphodiesterase 4 (PDE4) enzyme.

Said compounds inhibit the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3 and tumor necrosis factor-alpha (TNF-α). It also leads to an airway smooth muscle relaxation and a decrease in oedema.

The catalytic site of PDE4 has been previously identified: it mainly comprises a hydrophobic region in which two sub-pockets are present, e.g. $S_o$ and $S_1$, and a hydrophilic region containing the metal ions $Zn^{2+}$ and $Mg^{2+}$, that in turn comprises the sub-pocket $S_2$ spreading around the metal ions and a sub-pocket $S_3$ which branches approximately 90° from the middle of the hydrophobic pocket.

Most of the known compounds are provided with a moiety capable of interacting with the sub-pockets $S_0$ and $S_1$ of the hydrophobic region such as a substituted cathecol group and with another moiety able of indirectly interacting with the metal ions of the $S_2$ sub-pocket, for example a heterocycle such as pyridine or pyrrolidone.

The present invention is directed to compounds that can maintain the interactions with the sub-pockets $S_0$ and $S_1$ by means of the substituted catechol moiety and the interaction with the metal ions region by means of the pyridine ring like other known PDE4 inhibitors, but differing from them, for the presence of a sulfonylamino-benzoic acid group, which enable them to establish an additional interaction with the sub-pocket $S_3$.

In particular the present invention relates to compounds of formula (I) as defined earlier, including the pharmaceutically acceptable inorganic and organic salts, hydrates, solvates or addition complexes thereof.

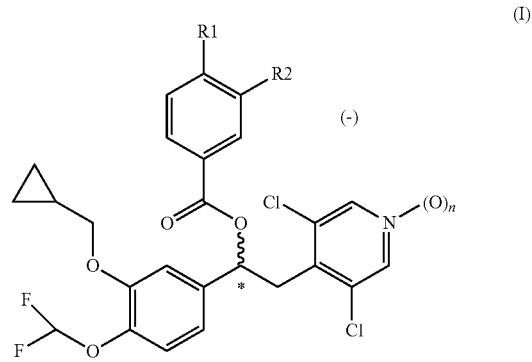

Preferred groups of compounds of formula (I) are those wherein:
R1 is —NHSO$_2$R4, R2 is —OR3, and n is 0;
R1 is —NHSO$_2$R4, R2 is —OR3, and n is 1;
R1 is —NHSO$_2$R4, wherein R4 is methyl, R2 is —OR3, wherein R3 is cyclopropylmethyl, and n is 0;
R1 is —NHSO$_2$R4, wherein R4 is methyl, R2 is —OR3, wherein R3 is cyclopropylmethyl, and n is 1;
R1 is linear or branched $C_1$-$C_6$ alkyl, R2 is —NHSO$_2$R4, and n is 0;
R1 is methyl, R2 is —NHSO$_2$R4, wherein R4 is methyl, and n is 0;
R1 is linear or branched $C_1$-$C_6$ alkyl, R2 is —NHSO$_2$R4, and n is 1;
R1 is methyl, R2 is —HNSO$_2$R4, wherein R4 is methyl, and n is 1;
R2 is linear or branched $C_1$-$C_6$ alkyl, R1 is —NHSO$_2$R4, and n is 0;
R2 is methyl, R1 is —HNSO$_2$R4, wherein R4 is methyl, and n is 0;
R2 is linear or branched $C_1$-$C_6$ alkyl, R1 is —NHSO$_2$R4, and n is 1;
R2 is methyl, R1 is —NHSO$_2$R4, wherein R4 is methyl, and n is 1;
R1 is —OR3, R2 is —NHSO$_2$R4, and n is 0;
R1 is —OR3, R2 is —NHSO$_2$R4, and n is 1;
R1 is —OR3 wherein R3 is cyclopropylmethyl, R2 is —NHSO$_2$R4 and R4 is methyl, and n is 1;
R1 is —OR3, R2 is —NHSO$_2$R4, and n is 1;
both R1 and R2 are —NHSO$_2$R4, and n is 0;

both R1 and R2 are —NHSO$_2$R4, wherein R4 is methyl, and n is 0;

both R1 and R2 are —NHSO$_2$R4, and n is 1; and both R1 and R2 are —NHSO$_2$R4, wherein R4 is methyl, and n is 1.

It will be apparent to those skilled in the art that compounds of formula (I) contain at least one asymmetric center, presently represented by the carbon atom with an asterisk, and therefore exist as optical stereoisomers.

The present invention is directed to the compounds of formula (I) which are (−) enantiomers with configuration (S) at the carbon atom represented with an asterisk.

The present invention is also directed to the intermediate compounds of formula (II) wherein the carbon atom represented with an asterisk has the (S) configuration.

The compounds of formula (I) show an in vitro inhibitory activity toward the PDE4 enzyme in the nM range, and they are endowed with a remarkable activity in the lungs upon intra-tracheal administration in an animal model of COPD.

They may also exhibit sustained pulmonary levels in the lungs, being undetectable in plasma, which is an index of a short systemic action.

According to preferred embodiments, the present invention provides the compounds of formula (I) reported below:

| Compound | Chemical name |
| --- | --- |
| C1 | (−)-3-Cyclopropylmethoxy-4-methanesulfonylamino-benzoic acid 1-(3-cyclopropylmethoxy-4-difluoromethoxy-phenyl)-2-(3,5-dichloro-pyridin-4-yl)-ethyl ester |
| C2 | (−)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| C3 | (−)-4-Cyclopropylmethoxy-3-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| C4 | (−)-3,4-Bis-methanesulfonylamino-benzoic acid 1-(3-cyclopropyl-methoxy-4-difluoromethoxy-phenyl)-2-(3,5-dichloro-1-oxy-pyridin-4-yl)-ethyl ester |
| C5 | (−)-3-Methanesulfonylamino-4-methyl-benzoic acid 1-(3-cyclopropyl-methoxy-4-difluoromethoxy-phenyl)-2-(3,5-dichloro-1-oxy-pyridin-4-yl)-ethyl ester |
| C6 | (−)-4-Methanesulfonylamino-3-methyl-benzoic acid 1-(3-cyclopropylmethoxy-4-difluoromethoxy-phenyl)-2-(3,5-dichloro-1-oxy-pyridin-4-yl)-ethyl ester |

The above compounds have been conveniently identified as (−) enantiomers which, however, have (S) configuration at the carbon atom marked with an asterisk. As such, these same compounds can be also identified as per the following table:

| Compound | Chemical name |
| --- | --- |
| C1 | 3-Cyclopropylmethoxy-4-methanesulfonylamino-benzoic acid 1-(S)-(3-cyclopropylmethoxy-4-difluoromethoxy-phenyl)-2-(3,5-dichloro-pyridin-4-yl)-ethyl ester |
| C2 | 3-Cyclopropylmethoxy-4-methanesulfonylamino-benzoic acid 1-(S)-(3-cyclopropylmethoxy-4-difluoromethoxy-phenyl)-2-(3,5-dichloro-1-oxy-pyridin-4-yl)-ethyl ester |
| C3 | 4-Cyclopropylmethoxy-3-methanesulfonylamino-benzoic acid 1-(S)-(3-cyclopropylmethoxy-4-difluoromethoxy-phenyl)-2-(3,5-dichloro-1-oxy-pyridin-4-yl)-ethyl ester |
| C4 | 3,4-Bis-methanesulfonylamino-benzoic acid 1-(S)-(3-cyclopropyl-methoxy-4-difluoromethoxy-phenyl)-2-(3,5-dichloro-1-oxy-pyridin-4-yl)-ethyl ester |
| C5 | 3-Methanesulfonylamino-4-methyl-benzoic acid 1-(S)-(3-cyclopropyl-methoxy-4-difluoromethoxy-phenyl)-2-(3,5-dichloro-1-oxy-pyridin-4-yl)-ethyl ester |
| C6 | 4-Methanesulfonylamino-3-methyl-benzoic acid 1-(S)-(3-cyclopropylmethoxy-4-difluoromethoxy-phenyl)-2-(3,5-dichloro-1-oxy-pyridin-4-yl)-ethyl ester |

Advantageously, the compounds of the invention are characterized by selectivity toward LPDE4 higher than that toward HPDE4, as obtained by the determination of their IC$_{50}$ values.

In the case of LPDE4, the IC$_{50}$ is the molar concentration of the test compound producing 50% inhibition of cAMP disappearance, assessed as described in Cortijo J et al., *Br. J. Pharmacol.*, 1993, 108: 562-568, which is incorporated herein by reference in its entirety. In the case of HPDE4 instead, the IC$_{50}$ is the molar concentration of the test compound producing 50% inhibition of the binding of [H$^3$] rolipram, assessed as described in Duplantier A J et al., *J. Med. Chem.*, 1996; 39: 120-125, which is also incorporated herein by reference in its entirety.

Preferably, the HPDE4/LPDE4 IC$_{50}$ ratio for the compounds of the invention is higher than 5, more preferably higher than 10, even more preferably higher than 20 and most preferably higher than 100.

The compounds of formula (I) may be prepared conventionally according to known methods. Some of the processes which can be used are described below and reported in Scheme 1.

Scheme 1
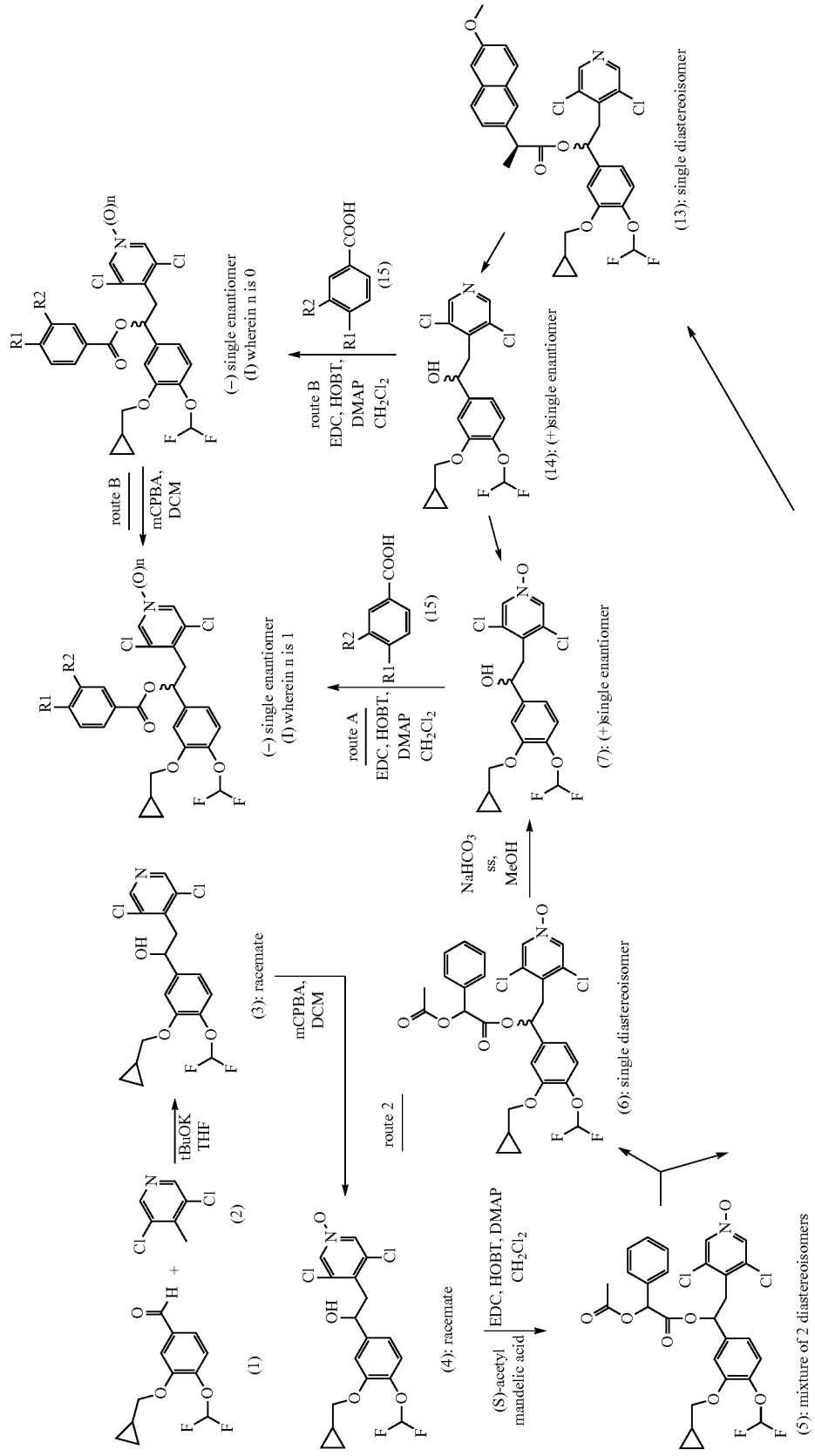

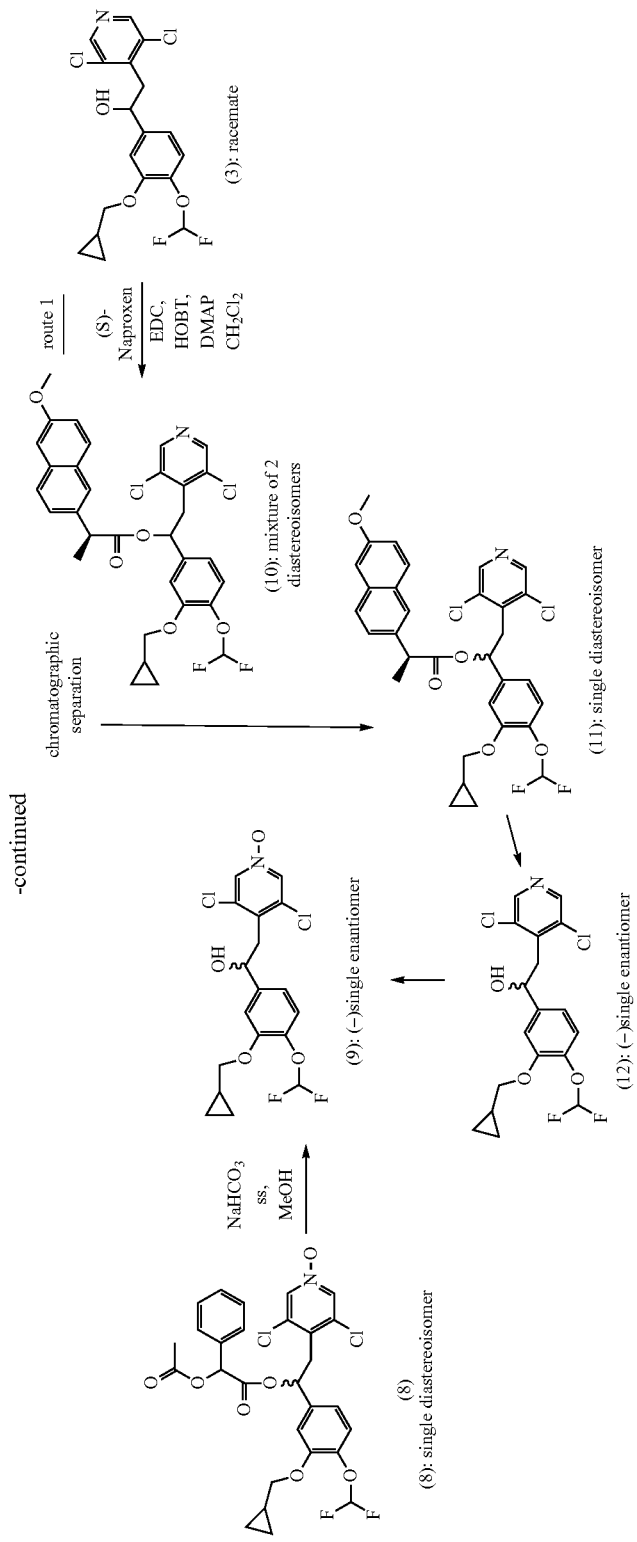

Procedure for the Preparation of Compounds of Formula (I)

According to a particular embodiment of the present invention, the compounds of formula (I) may be prepared, for example, following the synthetic pathways described in Scheme 1.

Racemic alcohol (3) may be prepared by reacting aldehyde (1) with methyldichloropyridine (2).

Route 1.

Racemic alcohol (3) may be separated into (−) (12) and (+) (14) enantiomers by known methods, such as by reacting the racemic mixture with a suitable chiral auxiliary thus obtaining a mixture of diastereoisomers. Such diastereoisomers may be separated by crystallization or by chromatography or by means of enzymes according to known methods. Subsequently, the chiral auxiliary may be removed from diastereoisomers to give the desired chiral alcohol as a single enantiomer. Alternatively, the alcohol racemic mixture may be resolved by means of chromatography with a chiral stationary phase, according to known methods (see, "Enantiomer Separation: Fundamentals and Practical Methods" F. Toda, Springer-Verlag 2004; and "Drug Stereochemistry: Analytical Methods and Pharmacology", Irving W. Wainer, CRC Press, 1993, which are both incorporated herein by reference in their entireties).

In particular, racemic alcohol (3) may be condensed with a chiral acid such as (S)-naproxen and the obtained diastereomeric mixture (10) may be separated into the two single diastereoisomers (11) and (13) by chromatography. After cleavage of the single diastereomeric esters by hydrolysis in an aqueous solvent or by alcoholysis in an alcoholic solvent, using acidic or basic conditions, enantiomeric pure alcohol intermediates (−) (12) and (+) (14) may be obtained.

Route 2.

Racemate (4), obtained by oxidation of racemate (3) carried out according to conventional methods, may be reacted with a chiral acid such as (S)-acetylmandelic acid so obtaining a mixture of two diastereoisomers (5). By trituration with diethyl ether and crystallization in a solvent such as isopropanol, ethanol or methanol, or by chromatographic separation, single diastereomeric esters (6) and (8) may be obtained.

After cleavage of single diastereomeric esters by hydrolysis in an aqueous solvent or by alcoholysis in an alcoholic solvent, using acidic or basic conditions, enantiomeric pure alcohol intermediates (+) (7) and (−) (9) may be obtained.

Compounds of formula (I) wherein n is 0 may be prepared by reacting the proper enantiomeric alcohol (+)(14) with benzoic acid (15) in the presence of a suitable strong base such as lithium diisopropylamide (LDA), NaH, or dimethylaminopyridine (DMAP) and in the presence of a condensing agent such as 1-Ethyl-3-[3-dimethylaminopropyl]-carbodiimide hydrochloride (EDC) or N-hydroxybenzotriazole (HOBT) in a solvent such as dichloromethane. Other solvents may be used, such as dimethylformamide (DMF), tetrahydrofuran (THF), chloroform, dioxane or any other aprotic solvent known to those skilled in the art. In a particular embodiment, the reaction may also be carried out in the absence of solvents.

Compounds of formula (I) wherein n is 1 may be prepared by oxidizing corresponding compounds of formula (I) wherein n is 0 by means of an oxidizing agent such as 3-chloroperbenzoic acid, peracetic acid or hydrogen peroxide in solvents such as chloroform, dichloromethane or acetic acid (route B).

Alternatively, compounds of formula (I) wherein n is 1 may also be prepared by first oxidizing alcohol enantiomers (+) (14), by means of the aforementioned operative conditions, thus obtaining alcohol enantiomers (+) (7). Subsequent reaction between the given alcohol enantiomer with a benzoic acid of formula (15), thus provides the above compounds of formula (I) wherein n is 0 (route A).

Separation of (+) (7) and (−) (9) enantiomers from racemic alcohol (4), which in its turn be obtained by oxidation of racemic alcohol (3), may be carried out by known methods, as described above for separation of enantiomers of racemic alcohol (3).

The skilled person should be aware that optional variations to the synthetic steps reported in scheme 1 may be applied as well to the preparation of the compounds of the invention.

In particular, the order of reactions may be performed so as to get the desired compounds or intermediates thereof, as well as to the choice of operative conditions being adapted, including solvents, optional oxidizing agents, condensing agents, and the like.

As an example, in case chemically reactive substituents are present in any of the starting materials or intermediates thereof, that might give rise to unwanted side reactions, suitable protection of those same substituents may be carried out before the reaction takes place.

By analogy, subsequent deprotection may be then carried out, so as to obtain again the above chemically reactive substituent or group in the free form.

The protection and deprotection of functional groups is described in "Protective Groups in Organic Chemistry," 3rd edition, T. W. Greene and P. G. M. Wuts, Wiley-Interscience (1999) and in "Protecting Groups," P. J. Kocienski, Georg Thieme Verlag (1994) both of which are incorporated herein by reference in their entireties.

According to the present process for the preparation of the compounds of the invention, and variants thereof, the starting materials of formula (1) and (2) as well as any additional reactant [(e.g. of formula (15)], auxiliar of chirality, solvent or agent being employed, is known or may be easily prepared according to known methods.

The present invention also provides pharmaceutical compositions of compounds of formula (I) in admixture with one or more pharmaceutically acceptable carriers, for example those described in Remington's Pharmaceutical Sciences Handbook, XVII Ed., Mack Pub., N.Y., U.S.A, which is incorporated herein by reference in its entirety.

Examples include diluents (such as sucrose, mannitol, lactose, starches) and known excipients, including suspending agents, solubilizers, buffering agents, binders, disintegrants, preservatives, colorants, flavours, lubricants and the like. Time release capsules, tablets and gels are also advantageous in administering the compounds of the present invention.

Administration of the compounds of the present invention may be accomplished according to patient needs, for example, orally, nasally, parenterally, e.g. subcutaneously, intravenously, intramuscularly, intrasternally and by infusion, by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders.

Various liquid oral dosage forms may also be used for administering compounds of the invention, including aqueous and non-aqueous solutions, emulsions, suspensions, syrups, and elixirs. Such dosage forms can also contain known suitable inert diluents such as water and known suitable excipients such as preservatives, wetting agents, sweeteners, flavours, as well as agents for emulsifying and/or suspending the compounds of the invention. The compounds of the invention may be injected, for example, intravenously, in the form of an isotonic sterile solution. Other preparations conventionally known in the art are also possible.

Suppositories for rectal administration of the said compounds of the invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, conventional carriers.

For topical administration, the pharmaceutical compositions may be in the form of creams, ointments, liniments, lotions, emulsions, suspensions, gels, solutions, pastes, powders, sprays, and drops suitable for administration to the skin, eye, ear or nose. Topical administration may also involve transdermal administration, e.g. by means of transdermal patches.

For the treatment of the diseases of the respiratory tract, the compounds of the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case, the powder may be filled in gelatine, plastic or other capsules, cartridges or blister packs or in a reservoir.

A diluent or carrier, generally chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with one or more other pharmaceutical active ingredients including those currently used in the treatment of respiratory disorders, e.g. $\beta_2$-agonists, corticosteroids and M3 antagonists.

The dosages of the compounds of the invention may depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) may be administered for example, at a dosage comprised between 0.001 and 1000 mg/day, preferably between 0.1 and 500 mg/day.

When they are administered by inhalation route, the dosage of the compounds of formula (I) is advantageously comprised between 0.01 and 20 mg/day, preferably between 0.1 and 10 mg/day.

Preferably, the compounds of formula (I) alone or combined with other active ingredients may be administered for the prevention and/or treatment of any obstructive respiratory disease such as asthma, chronic bronchitis and chronic obstructive pulmonary disease (COPD).

However the compounds of formula (I) may be administered for the prevention and/or treatment of any disease wherein the activity of PDE4 receptors is implicated and inhibition of PDE4 receptor activity is desired, or a disease state which is mediated by PDE4 activity (for instance a disease state in which PDE4 is overexpressed or overactive). Examples of such diseases include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, itching in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases, and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Example 1

Preparation of 1-(3-Cyclopropylmethoxy-4-difluoromethoxy-phenyl)-2-(3,5-dichloro-pyridin-4-yl)-ethanol (3)

A solution of 3-cyclopropylmethoxy-4-difluoromethoxy-benzaldehyde (5.00 g) and 3,5-dichloro-4-methylpyridine (2.57 g) in 50 ml dry THF was cooled to −30° C. Solid potassium t-butoxide (tBuOK, 1.96 g) was added portionwise maintaining the temperature between −30° C. and −20° C., thus obtaining a dark red solution. After completion of the addition, the mixture was stirred at −30° C. for 1 hour. A saturated aqueous solution of NH$_4$Cl (50 ml) was then added to the reaction mixture, maintaining the temperature between −5° C. and −10° C. The color of the reaction mixture turned to yellow.

The mixture was then extracted with EtOAc. The organic layer was dried over Na$_2$SO$_4$ and the solvent was removed by evaporation. The residue was treated with 30 ml of a mixture of petroleum ether/EtOAc=8/2; the precipitate was filtered and dried, obtaining 4.83 g of the title compound that was employed in the next step without further purification.

MS/ESI$^+$ 404-406 [MH]$^+$.

Example 2

Preparation of 1-(3-Cyclopropylmethoxy-4-difluoromethoxy-phenyl)-2-(3,5-dichloro-1-oxy-pyridin-4-yl)-ethanol (4)

Compound (3) (13.0 g) was dissolved in CH$_2$Cl$_2$ (250 ml) then m-chloro perbenzoic acid (16.5 g) was added, and the resulting solution was stirred at room temperature for 2 hours. Na$_2$S$_2$O$_3$ (25.4 g) was added, and the mixture was vigorously stirred at r.t. for 1 hour. The solid residue was filtered off, the solution was washed with 1N NaOH (3×100 ml) then the organic phase was dried over Na$_2$SO$_4$ and the solvent was removed by evaporation to give 10.3 g of the desired product (4) as a white solid that was used in the next steps without further purification.

MS/ESI$^+$ 420-422 [MH]$^+$

Example 3

Preparation of Acetoxy-phenyl-acetic acid 1-(3-cyclopropylmethoxy-4-difluoromethoxy-phenyl)-2-(3,5-dichloro-1-oxy-pyridin-4-yl)-ethyl ester (5, mixture of diastereoisomers)

Compound (4) (19.95 g), (S)-acetylmandelic acid (9.22 g), 1-ethyl-3-[3-dimethylamino propyl]carbodiimide hydrochloride (18 g), and 4-dimethylaminopyridine (2.89 g) were dissolved, under N$_2$ atmosphere, in dry CH$_2$Cl$_2$ (300 ml). The reaction mixture was stirred at room temperature overnight. A 5% aqueous solution of NaHCO$_3$ (200 ml) was added and the aqueous phase was extracted with CH$_2$Cl$_2$ (3×100 ml). The combined organic phases were dried over Na$_2$SO$_4$ and the solvent was evaporated under reduced pressure to give the title compound (5) as mixture of two diastereoisomers (32 g); separation of the two diastereoisomers is described in Examples 4 and 6.

Example 4

Preparation of (+)-Acetoxy-phenyl-acetic acid 1-(3-cyclopropylmethoxy-4-difluoromethoxy-phenyl)-2-(3,5-dichloro-1-oxy-pyridin-4-yl)-ethyl ester (6)

The crude diastereomeric mixture (5) (32 g) was triturated with Et$_2$O (100 ml), sonicated and filtered. The procedure was repeated four times in order to obtain a solid mixture enriched in diastereoisomer (6). This solid was crystallized from iPrOH (80 ml) and filtered to give 9.65 g of compound (6) with diastereomeric purity>95%. The diastereomeric purity was determined by HPLC analysis and by analytical chiral HPLC performed on Chiracel OD column (isocratic elution with hexane:isopropanol 40:60, flow 0.45 ml/min, retention time=27.2 min).

MS/ESI$^+$ 596, 598 [MH]

1H NMR (300 MHz, DMSO-d6) ppm 8.57 (s, 2H), 7.27-7.44 (m, 5H), 6.91-7.18 (m, 1H), 7.03 (t, 1H), 6.71-6.79 (m, 2H), 5.95 (dd, 1H), 5.85 (s, 1H), 3.72 (dd, 1H), 3.60 (dd, 1H), 3.41 (dd, 1H), 3.23 (dd, 1H), 2.13 (s, 3H), 1.07-1.31 (m, 1H), 0.48-0.72 (m, 2H), 0.21-0.44 (m, 2H)

[α]$_D$=+14° (c=0.54, MeOH)

Example 5

Preparation of (+)-1-(3-Cyclopropylmethoxy-4-difluoromethoxy-phenyl)-2-(3,5-dichloro-1-oxy-pyridin-4-yl)-ethanol (7)

Compound (6) (6.42 g) was suspended in methanol (350 ml) then a saturated solution of NaHCO$_3$ (175 ml) was added. The white suspension was vigorously stirred at room temperature overnight. The reaction mixture was diluted with CH$_2$Cl$_2$ (700 ml) and washed with a 5% aqueous solution of NaHCO$_3$ (300 ml); the aqueous phase was extracted with CH$_2$Cl$_2$ (2×300 ml), the combined organic layers were dried over Na$_2$SO$_4$, and the solvent was removed by evaporation under vacuum. The crude white solid obtained was triturated with Et$_2$O (2×100 ml) and filtered to give 3.88 g of compound (7) with enantiomeric purity>99%. The enantiomeric purity was determined by analytical chiral HPLC performed on Chiracel OD column (isocratic elution with hexane:isopropanol 30:70, flow 0.35 ml/min, retention time=22.3 min).

MS/ESI$^+$ 420-422 [MH]$^+$ $^1$H NMR (300 MHz, DMSO-d6) ppm 8.51 (s, 2H), 7.11 (d, 1H), 7.05 (d, 1H), 6.88 (dd, 1H), 7.01 (t, 1H), 5.59 (d, 1H), 4.84 (dd, 1H), 3.89 (dd, 1H), 3.84 (dd, 1H), 3.18 (dd, 1H), 3.02 (dd, 1H), 1.03-1.35 (m, 1H), 0.46-0.67 (m, 2H), 0.24-0.46 (m, 2H)

[α]$_D$=+68° (c=0.5, MeOH)

Example 6

Preparation of (+)-Acetoxy-phenyl-acetic acid 1-(3-cyclopropylmethoxy-4-difluoromethoxy-phenyl)-2-(3,5-dichloro-1-oxy-pyridin-4-yl)-ethyl ester (8)

The crude diastereomeric mixture (5) was triturated with Et$_2$O (100 ml), sonicated and filtered. The procedure was repeated four times, and the filtrates were collected and evaporated under reduced pressure to give a solid mixture enriched in diastereoisomer (8) that was crystallized from iPrOH (100 ml) to give 6.4 g of compound (8) as a white solid with diastereomeric purity>99%. The diastereomeric purity was determined by HPLC analysis and by analytical chiral HPLC performed on Chiracel OD column (isocratic elution with hexane:isopropanol 40:60, flow 0.45 ml/min, retention time=21.6 min).

MS/ESI$^+$ 596, 598 [MH]$^+$ $^1$H NMR (300 MHz, DMSO-d6) ppm 8.27 (s, 2H), 7.27-7.45 (m, 5H), 7.20 (d, 1H), 7.08 (d, 1H), 7.00 (dd, 1H), 7.08 (t, 1H), 5.97 (dd, 1H), 5.85 (s, 1H), 3.93 (dd, 1H), 3.89 (dd, 1H), 3.33 (dd, 1H), 3.17 (dd, 1H), 2.07 (s, 3H), 1.14-1.38 (m, 1H), 0.50-0.71 (m, 2H), 0.21-0.47 (m, 2H)

[α]$_D$=+26° (c=0.55, MeOH)

Example 7

Preparation of (−)-1-(3-Cyclopropylmethoxy-4-difluoromethoxy-phenyl)-2-(3,5-dichloro-1-oxy-pyridin-4-yl)-ethanol (9)

Compound (8) (1.18 g) was suspended in methanol (50 ml) then a saturated solution of NaHCO$_3$ (25 ml) was added. The white suspension was vigorously stirred at room temperature for 24 hours. The reaction mixture was diluted with CH$_2$Cl$_2$ (700 ml) then a 5% aqueous solution of NaHCO$_3$ (300 ml) was added, and the phases were separated. The aqueous phase was extracted with CH$_2$Cl$_2$ (2×100 ml), the combined organic layers were dried over Na$_2$SO$_4$, and the solvent was removed by evaporation under vacuum. The crude white solid obtained was triturated twice with Et$_2$O (50 ml) and once with CH$_2$Cl$_2$ (20 ml), then was filtered to give 0.74 g of compound (7) with enantiomeric purity>99%. The enantiomeric purity was determined by analytical chiral HPLC performed on Chiracel OD column (isocratic elution with hexane:isopropanol 30:70, flow 0.35 ml/min, retention time=24.0 min).

MS/ESI$^{+\ 420}$-422 [MH]$^+$ $^1$H NMR (300 MHz, DMSO-d6) ppm 8.51 (s, 2H), 7.11 (d, 1H), 7.05 (d, 1H), 6.88 (dd, 1H), 7.01 (t, 1H), 5.59 (d, 1H), 4.84 (dt, 1H), 3.89 (dd, 1H), 3.84 (dd, 1H), 3.18 (dd, 1H), 3.02 (dd, 1H), 1.08-1.32 (m, 1H), 0.47-0.66 (m, 2H), 0.26-0.45 (m, 2H)

[α]$_D$=−61° (c=0.5, MeOH)

Example 8

2-(6-Methoxy-naphthalen-2-yl)-propionic acid 1-(3-cyclopropylmethoxy-4-difluoromethoxy-phenyl)-2-(3,5-dichloro-pyridin-4-yl)-ethyl ester (10, mixture of diastereoisomers 11 and 13)

Compound (3) (12.0 g) was dissolved in DMF (100 ml) then (S)-2-(6-methoxy-naphthalen-2-yl)-propionic acid (7.5 g), 4-dimethylaminopyridine (3.6 g), and 1-ethyl-3-[3-dimethylaminopropyl]carbodiimide hydrochloride (5.7 g) was added. After stirring at rt for 4 hours, water (1000 ml) is added. The mixture was extracted with EtOAc (500 ml×2), the combined organic layers are dried over sodium sulphate, and the solvent was removed by evaporation under reduced pressure to afford 17.0 g of an oil which is crystallized from EtOH thus obtaining 11.5 g of the title compound as mixture of diastereomers (11) and (13), $^1$H NMR (200 MHz, CDCl$_3$) ppm 8.43 and 8.60 (2s, 1H each, 2H), 7.51-7.68 (m, 3H), 7.10-7.23 (m, 3H), 6.85-6.97 (m, 2H), 6.51-6.68 (m, 1H), 6.22-6.97 (t, 1H, CHF$_2$), 6.00-6.13 (m, 1H), 3.93-3.95 (s, 3H, OCH$_3$), 3.72-3.84 (m, 2H), 3.07-3.57 (m, 3H), 1.42-1.45 (d, 3H, CH$_3$), 0.94-1.25 (m, 1H), 0.51-0.67 (m, 2H), 0.12-0.36 (m, 2H).

MS/ESI$^+$ 616, 618 [MH]$^+$

Example 9

(+)-2-(6-Methoxy-naphthalen-2-yl)-propionic acid 1-(3-cyclopropyl methoxy-4-difluoromethoxy-phenyl)-2-(3,5-dichloro-pyridin-4-yl)-ethyl ester (second eluted diastereoisomer) (13)

The compound was isolated from the diastereomeric mixture of example 8 by HPLC separation using a Daisogel 10 μm, 50×300 mm column; eluent: n-hexane/methyl-tert-butyl-ether/isopropyl alcohol: 90/9.9/0.1; flow: 80 ml/min.; loading: 300 mg per injection; elution time: from 11 to 20 min. The collected fractions were evaporated and the residue was crystallized from n-hexane/isopropyl-alcohol.

$^1$H NMR (200 MHz, CDCl$_3$) ppm 8.60 (s, 2H), 7.68-7.75 (m, 2H), 7.58-7.59 (m, 1H), 7.27-7.29 (d, 1H), 7.12-7.24 (m, 2H), 6.98-7.04 (m, 1H), 6.73-6.78 (dd, 1H), 6.67-6.68 (d, 1H), 6.60-7.35 (t, 1H, CHF$_2$), 5.99-6.06 (m, 1H), 3.84-3.87 (m, 4H), 3.47-3.55 (m, 2H), 3.32-3.41 (dd, 1H), 3.22-3.29 (m, 1H), 1.33-1.37 (d, 3H, CH$_3$), 0.96-1.03 (m, 1H), 0.43-0.52 (m, 2H), 0.13-0.21 (m, 2H).

MS/ESI$^+$ 616, 618 [MH]$^+$ $[\alpha]_D$=+52.8° (c=0.5, MeOH)

Example 10

(+)-2-(6-Methoxy-naphthalen-2-yl)-propionic acid 1-(3-cyclopropylmethoxy-4-difluoromethoxy-phenyl)-2-(3,5-dichloro-pyridin-4-yl)-ethyl ester (first eluted diastereoisomer) (11)

The compound was isolated from the diastereomeric mixture of example 8 by HPLC separation using a Daisogel 10 μm, 50×300 mm column; eluent: n-exane/methyl-tert-butyl-ether/isopropyl-alcohol: 90/9.9/0.1; flow: 80 ml/min.; loading: 300 mg per injection; elution time: from 7 to 10 min. The collected fractions were evaporated and the residue was crystallized from n-hexane/isopropyl-alcohol.

$^1$H NMR (200 MHz, CDCl$_3$) ppm 8.27 (s, 2H), 7.64-7.80 (m, 2H), 7.56-7.57 (m, 1H), 7.28-7.29 (d, 1H), 7.14-7.20 (m, 3H), 6.68-7.42 (t, 1H, CHF$_2$), 6.93-6.98 (m, 2H), 6.00-6.07 (m, 1H), 3.88-3.92 (m, 4H), 3.71-3.84 (m, 2H), 3.39-3.51 (dd, 1H), 3.16-3.25 (dd, 1H), 1.33-1.37 (d, 3H, CH$_3$), 1.08-1.23 (m, 1H), 0.50-0.59 (m, 2H), 0.34-0.26 (m, 2H).

MS/ESI$^+$ 616, 618 [MH]$^+$ $[\alpha]_D$=+45° (c=0.5, MeOH)

Example 11

(+)-1-(3-Cyclopropylmethoxy-4-difluoromethoxy-phenyl)-2-(3,5-dichloro-pyridin-4-yl)-ethanol (14)

To a suspension of (+)-2-(6-methoxy-naphthalen-2-yl)-propionic acid-1-(3-cyclopropyl methoxy-4-difluoromethoxy-phenyl)-2-(3,5-dichloro-pyridin-4-yl)-ethyl ester (13) (14.0 g) in methanol (110 ml), potassium tert-butoxide (5.1 g) was added. The resulting mixture was stirred at rt for 2 hours, obtaining a clear solution. Water was slowly added under stirring to incipient precipitation (turbid solution).

After stirring for a further 60 minutes, the precipitated solid was filtered, washed with water and dissolved in chloroform (100 ml). The solution was dried over sodium sulphate and the solvent removed under vacuum. The residue was crystallized in chloroform/hexane=1/2.5 to obtain 8.1 g of white solid.

$^1$H NMR (200 MHz, CDCl$_3$) ppm δ 8.45 (s, 2H), 7.19-7.08 (d, 1H), 7.06-7.00 (d, 1H), 6.95-6.85 (dd, 1H), 6.99-6.24 (t, 1H, CHF$_2$), 5.18-5.00 (m, 1H), 3.98-3.78 (m, 2H), 3.54-3.35 (m, 1H), 3.31-3.15 (m, 1H), 2.04-1.94 (d, 1H, OH), 1.40-1.14 (m, 1H), 0.75-0.53 (m, 2H), 0.50-0.29 (m, 2H).

MS/ESI$^+$ 404, 406 [MH]$^+$.

$[\alpha]_D$=+9.35° (c=1, CHCl$_3$),

Example 12

(−)-1-(3-Cyclopropylmethoxy-4-difluoromethoxy-phenyl)-2-(3,5-dichloro-pyridin-4-yl)-ethanol (12)

Starting from diastereoisomer (11), following the procedure of Example 10, alcohol (12) was obtained.

MS/ESI$^+$ 404, 406 [MH]$^+$.

$[\alpha]_D$=−9.15° (c=1, CHCl$_3$).

Example 13

Preparation of Alcohol (7) by Oxidation of Alcohol (14)

Compound (14) (3.0 g) was dissolved in CH$_2$Cl$_2$ (100 ml). 70% m-Chloro perbenzoic acid (5.4 g) was added, and the resulting solution was stirred at room temperature for 18 hours. Solid Na$_2$S$_2$O$_3$ (5 g) was then added, and the mixture was vigorously stirred at r.t. for 30 minutes. The solid residue was removed by filtration; the organic solution was diluted with additional 100 ml of CH$_2$Cl$_2$ and washed with aqueous saturated NaHCO$_3$ solution (3×100 ml). The organic phase was dried over Na$_2$SO$_4$, and the solvent was removed by evaporation. The residue was triturated in EtOAc (20 ml) to give 1.9 g of the desired product 7 as a white solid, which was used in the next step without further purification.

$^1$H NMR (200 MHz, CDCl$_3$) ppm 8.14 (s, 2H), 7.18-7.09 (d, 1H), 7.07-7.02 (d, 1H), 6.92-6.83 (dd, 1H), 7.01-6.22 (t, 1H, CHF$_2$), 5.10-4.96 (m, 1H), 3.96-3.84 (d, 2H), 3.45-3.29 (m, 1H), 3.23-3.07 (m, 1H), 3.24-3.17 (d, 1H, OH), 1.41-1.67 (m, 1H), 0.75-0.53 (m, 2H), 0.50-0.29 (m, 2H).

MS/ESI$^+$ 420, 422 [MH]$^+$ $[\alpha]_D$=+65.0° (c=0.5, MeOH)

Example 14

Preparation of Alcohol (9) by Oxidation of Alcohol (12)

Alcohol (9) may be obtained following the procedure described in Example 13, using alcohol (12) in place of alcohol (14) as starting material.

MS/ESI+ 420, 422 [MH]+

$[\alpha]_D = -60.6°$ (c=0.5, MeOH)

Example 15

Preparation of (−)-3-Cyclopropylmethoxy-4-methanesulfonylamino-benzoic acid 1-(3-cyclopropylmethoxy-4-difluoromethoxy-phenyl)-2-(3,5-dichloro-1-pyridin-4-yl)-ethyl ester (C1)

Step 1: 3-Cyclopropylmethoxy-4-(N-tert-butoxycarbonyl-N-methanesulfonyl)-amino benzoic acid 1-(3-cyclopropylmethoxy-4-difluoromethoxy-phenyl)-2-(3,5-dichloro-pyridin-4-yl)-ethyl ester 1-Ethyl-3-[3-dimethylamino propyl]carbodiimide hydrochloride (2.85 g) was added to a solution of alcohol (14) (2.0 g), 4-dimethylaminopyridine (0.3 g), 3-cyclopropylmethoxy-4-(N-tert-butoxycarbonyl-N-methanesulfonyl)-amino-benzoic acid (2.0 g) in dry CH$_2$Cl$_2$ (180 ml) at r.t. under nitrogen atmosphere.

After stirring at r.t. overnight, the mixture was washed with 5% aqueous HCl (2×100 ml); the organic phase was separated and washed with a saturated aqueous solution of NaHCO$_3$ (2×100 ml), dried over Na$_2$SO$_4$ and evaporated to dryness. The crude was purified by flash chromatography on silica gel in gradient elution (hexane/EtOAc 10/1 to 6/4) to afford 1.4 g of the title compound.

Step 2: Preparation of C1

3-Cyclopropylmethoxy-4-(N-tert-butoxycarbony-N-methanesulfonyl)-amino-benzoic acid 1-(3-cyclopropylmethoxy-4-difluoromethoxy-phenyl)-2-(3,5-dichloro-pyridin-4-yl)-ethyl ester (1.4 g) was dissolved in CH$_2$Cl$_2$ (140 ml). A 4M solution of HCl in dioxane (40 ml) was added and the resulting mixture was stirred at r.t. for 24 hours. The reaction mixture was then evaporated to dryness, and the residue was triturated in iPrOH (50 ml) and subsequently in EtOH (50 ml) followed by Et$_2$O (70 ml) to afford 0.880 g of compound (C1).

Analytical characterization of C1 is reported in Table 1.

TABLE 1

| Compound | A | Analytical |
|---|---|---|
| C1 | (structure shown) | MS/ESI+ 671, 673 [MH]+; <br> 1H NMR (300 MHz, DMSO-d6) ppm 9.13 (br. s., 1 H) 8.60 (s, 2 H) 7.55 (dd, 1 H) 7.44-7.49 (m, 1 H) 7.39 (d, 1 H) 7.06 (t, 1 H) 6.78-7.33 (m, 3 H) 6.20-6.30 (m, 1 H) 3.87-3.98 (m, 4 H) 3.63-3.78 (m, 1 H) 3.38-3.50 (m, 1 H) 3.10 (s, 3 H) 1.09-1.40 (m, 2 H) 0.48-0.67 (m, 4 H) 0.28-0.44 (m, 4 H) <br> $[\alpha]_D = -22°$ (c = 0.4, MeOH) |

In the structure for A, *-indicates the position at which A is attached to the rest of the molecule.

Analogously, the following compounds may be prepared:

(−)-4-Cyclopropylmethoxy-3-methanesulfonylamino-benzoic acid 1-(3-cyclopropylmethoxy-4-difluoromethoxy-phenyl)-2-(3,5-dichloro-pyridin-4-yl)-ethyl ester;

(−)-3,4-Bis-methanesulfonylamino-benzoic acid 1-(3-cyclopropylmethoxy-4-difluoromethoxy-phenyl)-2-(3,5-dichloro-pyridin-4-yl)-ethyl ester;

(−)-3-Methanesulfonylamino-4-methyl-benzoic acid 1-(3-cyclopropylmethoxy-4-difluoromethoxy-phenyl)-2-(3,5-dichloro-pyridin-4-yl)-ethyl ester; and (−)-4-Methanesulfonylamino-3-methyl-benzoic acid 1-(3-cyclopropylmethoxy-4-difluoromethoxy-phenyl)-2-(3,5-dichloro-1-oxy-pyridin-4-yl)-ethyl ester.

Example 16

Preparation of (−)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester (C2)

Compound (C2) was prepared according to the same synthetic procedure of Example 15, starting from alcohol intermediate (7). Alternatively, compound (C2) can be prepared starting from compound (C1) as described in the following Example 17.

Example 17

Preparation of (−)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester (C2) starting from compound (C1)

Compound (C1) (0.69 g) was dissolved in $CH_2Cl_2$ (20 ml). 70% m-Chloro perbenzoic acid (0.355 g) was added, and the resulting solution was stirred at room temperature for 18 hours. Solid $Na_2S_2O_3$ (0.244 g) was then added, and the mixture was vigorously stirred at r.t. for 30 minutes. The solid residue was removed by filtration; the organic solution was diluted with additional 20 ml of $CH_2Cl_2$ and washed with aqueous saturated $NaHCO_3$ solution (3×20 ml). The organic phase was dried over $Na_2SO_4$ and the solvent was removed by evaporation. The residue was triturated in EtOH (20 ml) to give 0.710 g of the desired compound (C2) as a white solid.

The following compounds shown in Table 2 were prepared following the same route using suitable reagents.

TABLE 2

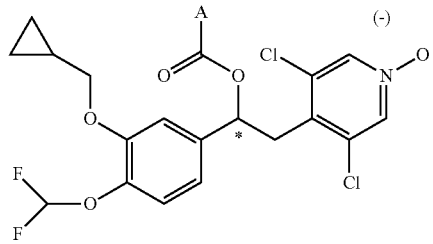

| Compound | A | Analytical |
|---|---|---|
| C2 | (structure: 4-methanesulfonylamino-3-cyclopropylmethoxy-phenyl) | MS/ESI$^+$ 687, 689 [MH]$^+$; $^1$H NMR (300 MHz, DMSO-d6) ppm 9.14 (br. s., 1 H), 8.56 (s, 2 H), 7.59 (dd, 1 H), 7.49 (d, 1 H), 7.41 (d, 1 H), 7.14-7.27 (m, 2 H), 7.07 (dd, 1 H), 7.06 (t, 1 H), 6.18 (dd, 1 H), 3.84-4.04 (m, 4 H), 3.61 (dd, 1 H), 3.34 (dd, 1 H), 3.11 (s, 3 H), 1.25-1.43 (m, 1 H), 1.13-1.26 (m, 1 H), 0.49-0.67 (m, 4 H), 0.27-0.47 (m, 4 H) [α]$_D$ = −47° (c = 0.4, MeOH) |
| C3 | (structure: 2-cyclopropylmethoxy-5-methanesulfonylamino-phenyl) | $^1$H NMR (200 MHz, CD$_3$OD-d4 calibrated at 3.31 ppm) δ ppm 8.42 (s, 2 H), 8.13 (d, J = 2.44 Hz, 1 H), 7.85 (dd, J = 8.79, 2.44 Hz, 1 H), 7.12-6.37 (t, 1H, CHF$_2$), 7.00-7.24 (m, 4 H), 6.26-6.40 (m, 1 H), 3.97 (dd, J = 14.89, 7.08 Hz, 4 H), 3.75 (dd, J = 13.92, 9.52 Hz, 1 H), 3.45 (dd, J = 14.16, 4.39 Hz, 1 H), 2.98 (s, 3 H), 1.17-1.45 (m, 2 H), 0.54-0.75 (m, 4 H), 0.29-0.47 (m, 4 H) [α]$_D$ = −36 (c = 0.1, CHCl$_3$) |
| C4 | (structure: bis-methanesulfonylamino phenyl) | $^1$H NMR (200 MHz, CDCl$_3$ calibrated at 7.26 ppm) δ ppm 8.23 (s, 2 H), 7.85-8.01 (m, 2 H), 7.69 (d, J = 8.30 Hz, 1 H), 7.20 (m, 1 H), 7.00-6.25 (t, 1H, CHF$_2$), 6.97-7.11 (m, 2 H), 6.21-6.32 (m, 1 H), 3.91 (d, J = 6.84 Hz, 2 H), 3.72 (dd, J = 13.67, 10.74 Hz, 1 H), 3.32 (dd, J = 13.92, 3.66 Hz, 1 H), 3.04 (d, J = 17.58 Hz, 6 H), 1.16-1.35 (m, 1 H), 0.55-0.74 (m, 2 H), 0.30-0.45 (m, 2 H) [α]$_D$ = −27 (c = 0.1, CHCl$_3$) |
| C5 | (structure: 2,5-dimethyl-methanesulfonylamino phenyl) | $^1$H NMR (200 MHz, DMSO-d6 calibrated at 2.50 ppm) δ ppm 9.25 (s, 1 H), 8.53 (s, 2 H), 7.91 (m, 1 H), 7.76 (d, J = 8.30 Hz, 1 H), 7.43-6.69 (t, 1H, CHF$_2$), 7.40 (d, J = 8.30 Hz, 1 H), 7.19 (d, J = 4.39 Hz, 2 H), 7.00-7.12 (m, 1 H), 6.21 (dd, J = 9.52, 4.15 Hz, 1 H), 3.92 (d, J = 6.84 Hz, 2 H), 3.63-3.55 (m, 1 H), 3.37 (d, J = 4.39 Hz, 1 H), 2.99 (s, 3 H), 2.37 (s, 3 H), 1.11-1.28 (m, 1 H), 0.48-0.65 (m, 2 H), 0.26-0.41 (m, 2 H) [α]$_D$ = −38.67° |
| C6 | (structure: 2-methyl-4-methanesulfonylamino phenyl) | $^1$H NMR (200 MHz, DMSO-d6 calibrated at 2.50 ppm) δ ppm 8.55 (s, 2 H), 7.93-7.83 (m, 2 H), 7.49 (d, J = 8.30 Hz, 1 H), 7.43-6.69 (t, 1H, CHF$_2$), 7.03-7.27 (m, 3 H), 6.11-6.24 (m, 1 H), 3.93 (d, J = 6.84 Hz, 2 H), 3.60 (s, 3 H), 2.28 (s, 3 H), 1.11-1.29 (m, 1 H), 0.57 (m, 2 H), 0.34 (m, 2 H) [α]$_D$ = −58.0° |

In the structure for A, *-indicates the position at which A is attached to the rest of the molecule.

The carboxylic acid intermediates employed in the synthesis of the described final compounds are commercially available or are already known or are synthesized according to known methods.

Example 18

Synthesis of 3-Cyclopropylmethoxy-4-(N-tert-butoxycarbonyl-N-methane-sulfonyl)-amino-benzoic acid Scheme 2

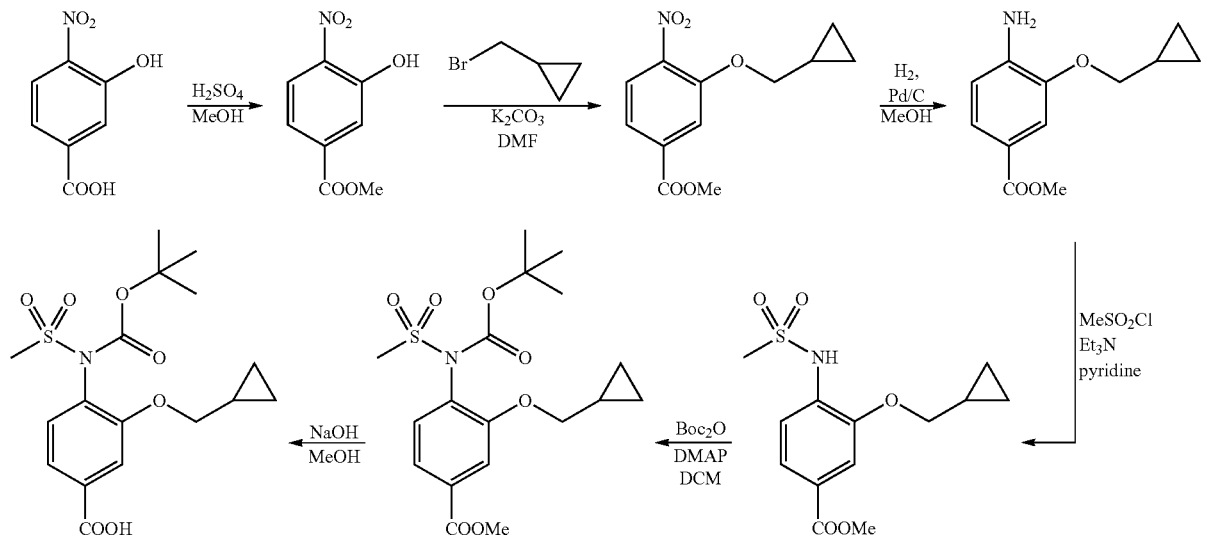

Step 1: 3-Hydroxy-4-nitro-benzoic acid methyl ester

3-Hydroxy-4-nitro-benzoic acid (10 g) was dissolved in MeOH (500 ml). 96% $H_2SO_4$ (2 ml) was added, and the mixture was heated to 60° C. for 18 hours. The reaction mixture was concentrated to approx. 200 ml, diluted with EtOAc (200 ml) and washed with an aqueous saturated solution of $NaHCO_3$ (2×20 ml). The organic layer was dried over $Na_2SO_4$ and the solvent was removed by evaporation to yield 10.5 g of the desired intermediate.

Step 2: 3-Cyclopropylmethoxy-4-nitro-benzoic acid methyl ester

3-Hydroxy-4-nitro-benzoic acid methyl ester (10.5 g) was dissolved in dry DMF (150 ml) under $N_2$ atmosphere. $K_2CO_3$ (24.3 g), KI (2.6 g) and yclopropylmethylbromide (10.3 ml) were added and the mixture was stirred at 50° C. for 6 hours. The reaction mixture was diluted with water (300 ml) and extracted with $Et_2O$ (2×200 ml); the combined organic layers were dried over $Na_2SO_4$ and the solvent was removed by evaporation to yield 12.7 g of the desired intermediate.

Step 3: 4-Amino-3-cyclopropylmethoxy-benzoic acid methyl ester

3-Cyclopropylmethoxy-4-nitro-benzoic acid methyl ester (12.7 g) was dissolved in MeOH (100 ml) and EtOAc (100 ml); 10% Pd/C (1.0 g, suspended in 20 ml of water) was added, and the mixture is hydrogenated in a Parr apparatus ($H_2$: 20 psi) for 5 hours. 37% HCl was added (10 ml), and hydrogenation was continued for additional 2 hours to obtain complete conversion. The catalyst was filtered over a celite pad, the mixture was diluted with EtOAc (200 ml) and washed with an aqueous saturated solution of $NaHCO_3$ (2×100 ml). The organic layer was dried over $Na_2SO_4$ and the solvent was removed by evaporation to yield 10.7 g of the desired intermediate.

Step 4: 3-Cyclopropylmethoxy-4-methanesulfonylamino-benzoic acid methyl ester Methyl 3-(cyclopropylmethoxy)-4-aminobenzoate (8.86 g) was dissolved in pyridine (80 mL) at room temperature under $N_2$ atmosphere. Methanesulfonyl chloride (4.04 mL) was added and the mixture was stirred at r.t. for 18 hours. The reaction mixture was evaporated to dryness, the crude was treated with 1N HCl (500 mL) and extracted with $CH_2Cl_2$ (3×200 mL). The organic layer was dried over $Na_2SO_4$ and the solvent was evaporated off to yield 11.7 g of the desired intermediate.

MS/ESI$^+$ 300 [MH]$^+$

Step 5: 3-Cyclopropylmethoxy-4-(N-tert-butoxycarbonyl-N-methanesulfonyl)-amino-benzoic acid methyl ester 3-Cyclopropylmethoxy-4-methanesulfonylamino-benzoic acid methyl ester (3.0 g) was dissolved in $CH_2Cl_2$ (150 ml). Dimethylaminopyridine (DMAP, 1.22 g) and $Boc_2O$ (2.18 g) were added and the mixture was stirred at r.t. for 1 hour. The reaction mixture was washed with 5% aqueous HCl (2×50 ml), the organic layer was dried over $Na_2SO_4$ and the solvent was removed by evaporation. The residue was triturated in $Et_2O$ and filtered to afford 4.0 g of the desired intermediate that was used in the next steps without further purification.

Step 6: 3-Cyclopropylmethoxy-4-(N-tert-butoxycarbonyl-N-methanesulfonyl)-amino-benzoic acid Cyclopropylmethoxy-4-(N-tert-butoxycarbonyl-N-methanesulfonyl)-amino-benzoic acid methyl ester (4.0 g) was dissolved in MeOH (100 ml). 1N NaOH (15 ml) was added, and the resulting mixture was stirred at r.t. for 1 hour, then was heated to 50° C. for 2 hours. The reaction mixture was then diluted with EtOAc (250 ml) and washed with 1N HCl (2×100 ml). The organic layer was dried over $Na_2SO_4$ and the solvent was evaporated off to give 3.5 g of the desired acid derivative.

MS/ESI⁺ 386 [MH]⁺.

Legend
*NMR
s=singlet
d=doublet
t=triplet
q=quartet
dd=doublet of doublets
m=multiplet
br=broad
ESI=electrospray
Pharmacological Activity of the Compounds of the Invention

Example 19

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), is performed according to a method previously described (Hatzelmann A et al., *J. Pharmacol. Exp. Ther.*, 2001; 297:267-279; and Draheim R et al., *J. Pharmacol. Exp. Ther.*, 2004; 308: 555-563, both of which are incorporated herein by reference in their entireties.

Cryopreserved human PBMCs, (100 μl/well) are incubated in 96-well plates ($10^5$ cells/well), for 30 minutes, in the presence or absence (50 microl) of the test compounds whose concentrations range from $10^{-12}$ M to $10^{-6}$ M. Subsequently, LPS (3 ng/ml) is added.

After 18 hours incubation at 37° C. in a humidified incubator under an atmosphere of 95% air and 5% $CO_2$, culture medium is collected and TNF-α is measured by ELISA.

The results regarding compounds C1 to C6, expressed as mean±95% confidence limits of the molar concentration of the test compound producing 50% inhibition of LPS-induced TNF-α release ($IC_{50}$), are comprised between 0.06 and 4.4 nM. The effects of the tested compounds are calculated as percentage of inhibition of TNF-α release, assuming LPS-induced TNF-α production in the absence of inhibitor compound as 100% and basal TNF-α production of PBMCs in the absence of LPS as 0%.

Example 20

Evaluation of the Ability to Inhibit the Low Affinity LPDE4 Versus the Ability to Compete for the High Affinity HPDE4

The affinity toward LPDE4 and HPDE4 is assessed as previously described respectively in Cortijo J et al., *Br. J. Pharmacol.*, 1993, 108: 562-568 and Duplantier A J et al., *J. Med. Chem.*, 1996; 39: 120-125, both of which are incorporated herein by reference in their entireties.

The concentration of the test compound ranges between $10^{-12}$ M and $10^{-5}$ M. The values of affinity toward LPDE4 and HPDE4 tested on compounds C1 to C6 are comprised between 82 and 477.

In the case of LPDE4, the $IC_{50}$ is the molar concentration of the test compound producing 50% inhibition of cAMP disappearance, while in the case of HPDE4, the $IC_{50}$ is the molar concentration of the test compound producing 50% inhibition of the binding of [$H^3$] rolipram.

The results indicate that the compounds of the invention inhibit LPDE4 with subnanomolar affinity and are considerably more selective toward LPDE4 versus HPDE4.

Example 21

Synergistic Activity of Fixed Dose Combination of Carmoterol/C1 on Carbachol-Induced Contraction in Guinea-Pigs Trachea Zig-zag tracheal segments are obtained from male Ovoalbumin(OA)-sensitized guinea pigs and two preparations are obtained from a trachea. Each preparation is placed in 20-ml organ bath filled with oxygenated ($O_2$ 95% and $CO_2$ 5%) normal Krebs-Henseleit solution and maintained at 37° C. Tracheal preparations are connected to isometric force transducers under a resting tone of 1 g. After an equilibration period of 60 minutes, tracheal preparations are pretreated for 30 minutes with C1 (10-7 M), Carmoterol (3*10-10 M), the association C1 and Carmoterol or vehicle, respectively, followed by cumulative administration of OA ($10^{-10}$-$10^{-5}$ g/ml). At the end of the OA administration a maximal concentration of carbachol ($10^{-5}$ M) is added to obtain the maximal contraction of each preparation. The effects are expressed as percent values of the carbachol-induced maximal response (100%).

30-Minute pre-treatment of the preparation with C1 ($10^{-7}$ NI) caused an inhibition of the OA-induced contraction of 23%. Similarly the inhibition produced by Carmoterol (3*10-10 M) is 18%.

C1 (10-7 M) and Carmoterol (3*$10^{-10}$ M)-combination caused a reduction of the OA-induced contraction of the 93%.

This study shows that both carmoterol and C1 are potent in antagonizing carbachol-induced contraction in guinea-pig airways. Moreover, in line with their complementary molecular mechanism of action, in the frame of a functional agonism-antagonism, fixed combinations display synergistic effect in the control of cholinergic contraction in guinea-pig trachealis Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of treating a disease of the respiratory tract characterized by airway obstruction, comprising administering, to a subject in need thereof, an effective amount of a compound of formula (I) as an (−) enantiomer

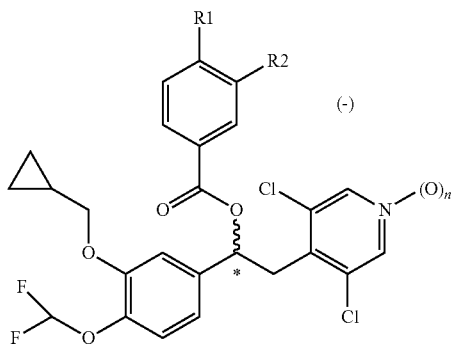

wherein:

n is 0 or 1;

R1 and R2 may be the same or different, and are selected from the group consisting of:

linear or branched $C_1$-$C_6$ alkyl, optionally substituted by one or more halogen atoms;

—OR3 wherein R3 is a linear or branched $C_1$-$C_6$ alkyl optionally substituted with one or more halogen atoms or $C_3$-$C_7$ cycloalkyl groups; and —NHSO$_2$R4 wherein R4 is a linear or branched $C_1$-$C_4$ alkyl optionally substituted with one or more halogen atoms, wherein at least one of R1 and R2 is —NHSO$_2$R4, or a pharmaceutically acceptable salt thereof.

2. A method according to claim 1, wherein R1 is —NHSO$_2$R4, wherein R4 is methyl, R2 is —OR3, wherein R3 is cyclopropylmethyl, and n is 0.

3. A method according to claim 1, wherein R1 is —NHSO$_2$R4, wherein R4 is methyl, R2 is —OR3, wherein R3 is cyclopropylmethyl, and n is 1.

4. A method according to claim 1, wherein R1 is —OR3, R2 is —NHSO$_2$R4 wherein R4 is methyl, and n is 1.

5. A method according to claim 1, wherein R1 is methyl, R2 is —NHSO$_2$R4 wherein R4 is methyl, and n is 1.

6. A method according to claim 1, wherein both R1 and R2 are —NHSO$_2$R4, wherein R4 is methyl, and n is 0.

7. A method according to claim 1, wherein both R1 and R2 are —NHSO$_2$R4, wherein R4 is methyl, and n is 1.

8. A method according to claim 1, further comprising administering a second pharmaceutical active component selected from the group consisting of a β2 agonist, an M3 antagonist, and a corticosteroid.

9. A method according to claim 8, wherein said second active component is formoterol or carmoterol.

10. A method according to claim 1, comprising administering a pharmaceutical composition comprising a compound of formula (I) or a salt thereof and one or more pharmaceutically acceptable carriers and/or excipients.

11. A method according to claim 1, comprising administering a pharmaceutical composition comprising:
a compound of formula (I) or a salt thereof;
a second pharmaceutical active component selected from the group consisting of a β2 agonist, an M3 antagonist, and a corticosteroid; and
one or more pharmaceutically acceptable carriers and/or excipients.

12. A method according to claim 10, wherein said administering is carried out with a device which is a single- or multi-dose dry powder inhaler, a metered dose inhaler, or a soft mist nebulizer.

13. A method according to claim 11, wherein said administering is carried out with a device which is a single- or multi-dose dry powder inhaler, a metered dose inhaler, or a soft mist nebulizer.

14. A method according to claim 1, wherein said disease of the respiratory tract characterized by airway obstruction is asthma.

15. A method of preventing and/or treating atopic dermatitis, comprising administering an effective amount of a compound of formula (I) or a salt thereof according to claim 1, wherein said disease of the respiratory tract characterized by airway obstruction is COPD.

16. A method according to claim 2, wherein said disease of the respiratory tract characterized by airway obstruction is asthma.

17. A method according to claim 2, wherein said disease of the respiratory tract characterized by airway obstruction is COPD.

18. A method according to claim 3, wherein said disease of the respiratory tract characterized by airway obstruction is asthma.

19. A method according to claim 3, wherein said disease of the respiratory tract characterized by airway obstruction is COPD.

20. A method according to claim 4, wherein said disease of the respiratory tract characterized by airway obstruction is asthma.

21. A method according to claim 4, wherein said disease of the respiratory tract characterized by airway obstruction is COPD.

* * * * *